US009067958B2

(12) United States Patent
Romero

(10) Patent No.: US 9,067,958 B2
(45) Date of Patent: Jun. 30, 2015

(54) SCALABLE AND HIGH YIELD SYNTHESIS OF TRANSITION METAL BIS-DIAZABUTADIENES

(71) Applicant: Intel Corporation, Santa Clara, CA (US)

(72) Inventor: Patricio E. Romero, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 34 days.

(21) Appl. No.: 14/053,249

(22) Filed: Oct. 14, 2013

(65) Prior Publication Data

US 2015/0105573 A1   Apr. 16, 2015

(51) Int. Cl.
| | | |
|---|---|---|
| C07F 15/00 | (2006.01) | |
| C07F 11/00 | (2006.01) | |
| C23C 16/18 | (2006.01) | |
| C07F 15/06 | (2006.01) | |
| C07F 15/02 | (2006.01) | |
| C07F 15/04 | (2006.01) | |

(52) U.S. Cl.
CPC ............ C07F 15/065 (2013.01); C07F 15/025 (2013.01); C07F 15/045 (2013.01); C23C 16/18 (2013.01)

(58) Field of Classification Search
CPC .... C07F 11/005; C07F 15/025; C07F 15/045; C07F 15/065; C23C 16/18

USPC ................................... 556/35; 427/252
See application file for complete search history.

(56) References Cited

U.S. PATENT DOCUMENTS

| | | | |
|---|---|---|---|
| 6,020,511 A | 2/2000 | Vaartstra et al. | |
| 2013/0164456 A1 | 6/2013 | Winter et al. | |
| 2013/0251903 A1* | 9/2013 | Han | ............................ 427/252 |
| 2014/0235054 A1* | 8/2014 | Lansalot-Matras et al. | .. 438/681 |
| 2014/0363575 A1* | 12/2014 | Thompson et al. | .... 427/255.394 |

OTHER PUBLICATIONS

Cloke et al., "Synthesis and Reactivity of bis(η-1,4-Di-tert-butylbuta-1,3-diene)cobalt; the X-Ray Crystal Structure of the Anionic Butadiene Sandwich Complex [K( 18-crown-6)(thf)2][Co(η-C4H4But2) 2]", J. Chem. Soc., Chem. Commun., 1993.
Kinsley, et al., "Volatility and High Thermal Stability in Mid- to Late-First-Row Transition-Metal Diazadienyl Complexes", pubs.acs.org/Organometallics, Aug. 25, 2011.

* cited by examiner

*Primary Examiner* — Porfirio Nazario Gonzalez
(74) *Attorney, Agent, or Firm* — Grossman, Tucker, Perreault & Pfleger, PLLC

(57) ABSTRACT

The present disclosure is directed at the synthesis of transition metal bis-diazabutadienes as precursors to enable atomic layer deposition (ALD) or chemical vapor deposition (CVD) of transition metals on metallic surfaces. The transition metal bis-diazabutadienes may be prepared in a two-step synthetic procedure at relatively high yields and are particularly suitable for industrial scale-up.

7 Claims, 2 Drawing Sheets

SCALABLE AND HIGH YIELD SYNTHESIS OF TRANSITION METAL BIS-DIAZABUTADIENES

FIELD

The present disclosure is directed at the synthesis of transition metal bis-diazabutadienes as precursors to enable atomic layer deposition (ALD) or chemical vapor deposition (CVD) of transition metals on metallic surfaces.

BACKGROUND

Transition metal bis-diazabutadienes [(DABD)$_2$M] have been previously identified as precursors that enable the selective ALD or CVD of transition metals on metallic surfaces. See, C. Winter et al, *Organometallics* 2011, 30, 5010-5017. In addition, (DABD)$_2$M precursors avoid deposition on adjacent dielectric surfaces such as SiO$_2$ or low dielectric constant organic interlayer dielectrics (low-k ILDs). This selectivity is a characteristic of the chemical make-up of the (DABD)$_2$M precursors and chemical passivation of the undesired surface may not be required. However, existing methods of preparation of M-DABD are relatively low yielding and plagued by the formation of undesired by-products (Winter et al).

The growth of material layers by ALD generally involves the following steps: (1) exposure of the substrate to a first precursor of an organometallic compound that modifies the substrate surface; (2) purge or evacuation of the reaction chamber to remove non-reacted precursors and other gaseous reaction by-products; (3) exposure to a second gaseous chemical composition that reacts with the modified substrate surface to form a film. A purging gas may then be introduced to remove any residual second chemical composition and the steps may be repeated.

BRIEF DESCRIPTION

The above-mentioned and other features of this disclosure, and the manner of attaining them, may become more apparent and better understood by reference to the following description of embodiments described herein taken in conjunction with the accompanying drawings, wherein.

DETAILED DESCRIPTION

The present disclosure is directed at methods of synthesizing, at relatively high yields, molecular precursors to enable ALD or CVD of transition metals on metallic surfaces. The molecular precursors fall generally in the category of transition metal bis-diazabutadiene complexes. The transition metals may therefore include transition metals selected from Groups 3-7 of the periodic table. Preferably, the transition metal includes Fe, Co, Ni or Cr. The precursors so prepared at relatively high yields may then be conveniently employed in ALD or CVD coating procedures.

Figure 1:
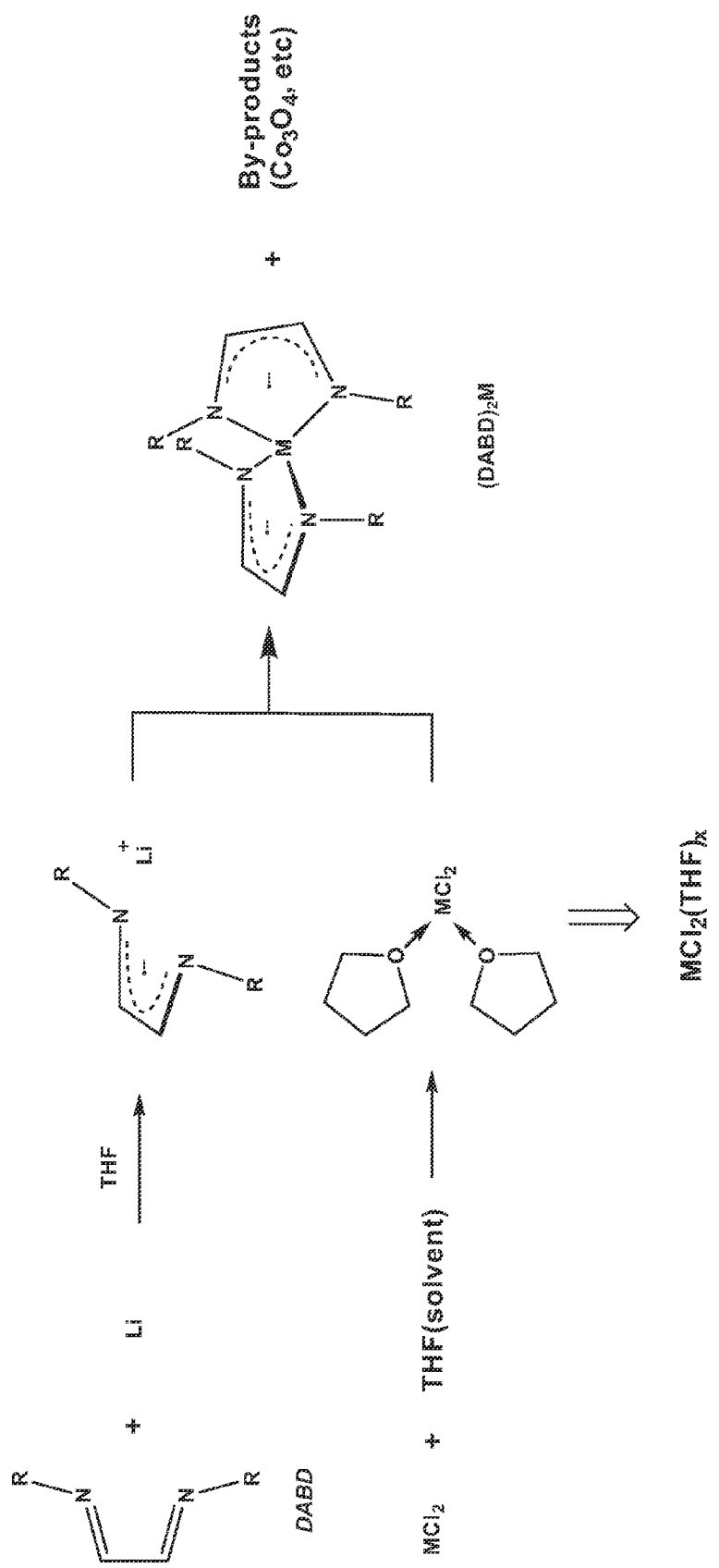
FIG. 1 illustrates a reported one-step synthesis of (DABD)$_2$M complex via the reaction of DABD, metal chloride and lithium metal in tetrahydrofuran (TFH).

FIG. 1 illustrates a reported synthesis of (DABD)$_2$M via the indicated one-step reaction of DABD ligand, metal chloride and lithium metal in THF. See, U.S. Patent Appl. Publ. No 2013/0164456; Winter et al, noted above. This one-step reaction provides the indicated (DABD)$_2$M precursor at yields of 36-47% for that situation where M=Cr, Fe, Co or Ni. In the case of Mn, yields of 81% are indicated. The relatively low yields noted above for Cr, Fe, Co or Ni appears to be related to the fact that corresponding metal chlorides that are employed to provide such metals (M) in the final (DABD)$_2$M complex may retain THF in their coordination sphere, forming initial solvates of the form MCl$_2$(THF)$_x$ (FIG. 1). When lithium and DABD ligand are added to the mixture, differences in the reaction kinetics make the reduction of these THF solvates competitive with the one-electron reduction of the DABD by lithium. Alternatively, the reduced DABD ligand could also act as the direct reducing agent given its higher solubility compared to Li metal in this medium. The undesired reduction of the THF solvate has been experimentally confirmed for M=Co. As a result, the one-step protocol whereby DABD is exposed to THF, CoCl$_2$ and lithium leads to the formation of insoluble and darkened by-products (presumably mixtures of cobalt oxides), and relatively low yields of 36-47% when M=Cr, Fe, Co or Ni.

Figure 2:
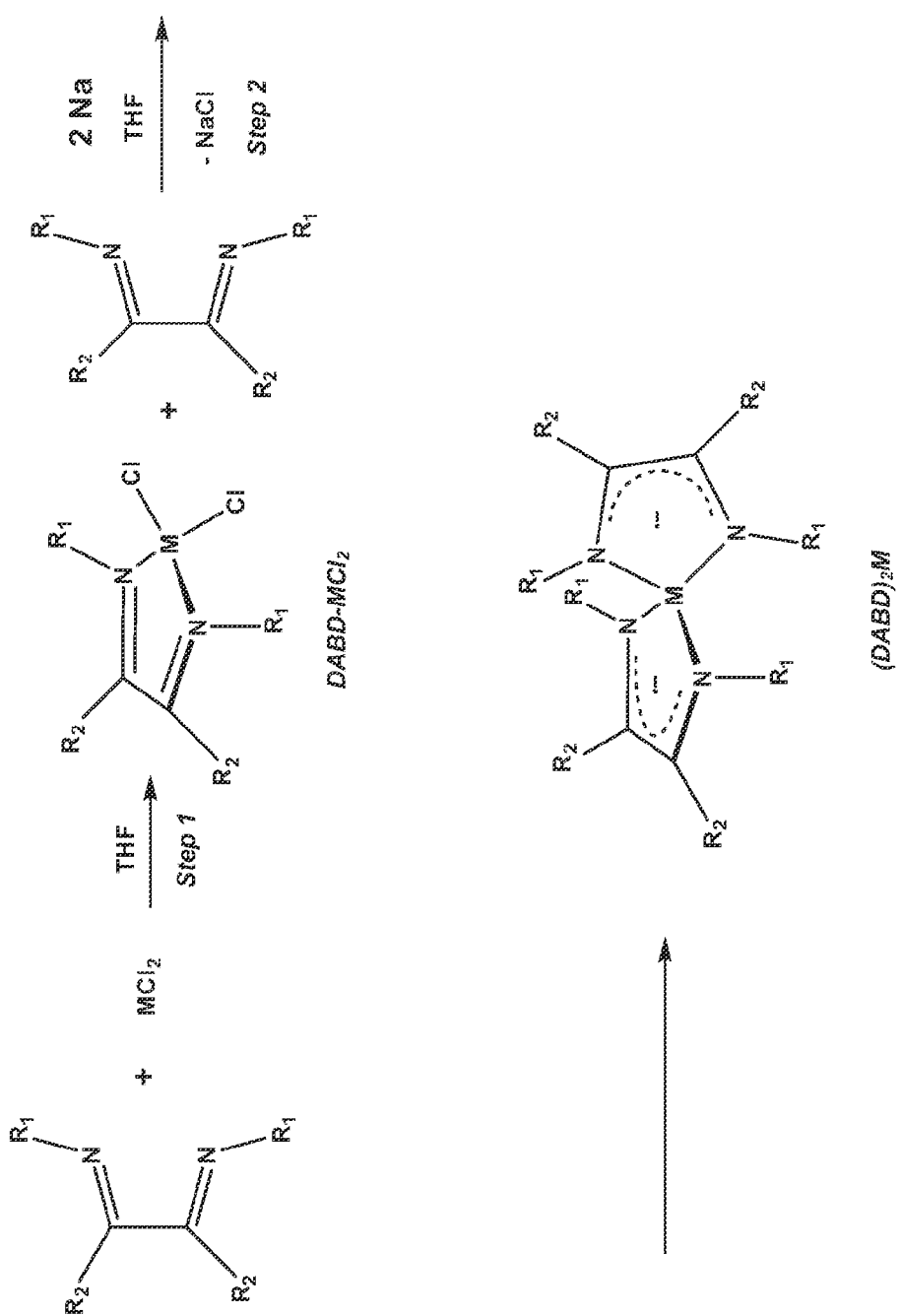
FIG. 2 illustrates a two step method for synthesis of a (DABD)$_2$M complex.

The present disclosure therefore provides what may be described as a two step procedure for the production of transition metal bis-diazabutadienes. Attention is directed to the scheme illustrated in FIG. 2. In a first step, DABD is treated with a transition metal halide (cobalt chloride as the illustrated example) in THF solvent at reflux for approximately 12 hours. The halide portion may be a chlorine, bromine or iodine atom.

As illustrated, the DABD may include R$_1$-group substitution on the indicated nitrogen atom where R$_1$ may by a C$_1$-C$_{12}$ alkyl group, amine or a C$_6$-C$_{18}$ aryl group. R$_2$-group substitution on the indicated carbon atoms of the DABD may include hydrogen, a C$_1$-C$_{10}$ alkyl, a C$_6$-C$_{18}$ aryl group, amino, C$_1$-C$_{12}$ alkylamino or a C$_2$-C$_{24}$ dialkylamino. When the DABD ligand is treated with MCl$_2$ in this fashion, without reducing agent (e.g. lithium) present, the product formed is comprised of a complex of the form (DABD)MCl$_2$. One particularly preferred DABD-transition metal halide complex formed in the first step comprises the reaction of CoCl$_2$ with N,N'-ditertbutyl-1,4-diazabutadiene in refluxing THF, which has the following structure:

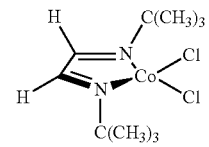

The structure depicted above was confirmed by single crystal X-ray crystallography.

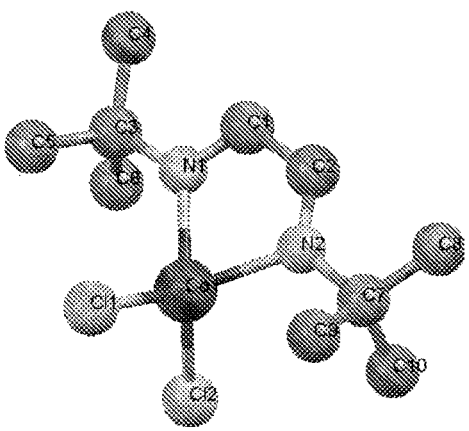

Selected Bond Distances and Angles:

Distances (Å): Co(1)-N(1) 2.0538(12); Co(1)-N(2) 2.0601 (12); Co(1)-Cl(2) 2.2171(4); Co(1)-Cl(1) 2.2194(4); N(1)-C (1) 1.2726(18); N(2)-C(2) 1.2675(19). Angles (°): N(1)-Co (1)-N(2) 81.74(5); N(1)-Co(1)-Cl(2) 117.89(4); N(2)-Co(1)-Cl(2) 115.73(3); N(1)-Co(1)-Cl(1) 112.44(4); N(2)-Co(1)-Cl (1) 112.30(3); Cl(2)-Co(1)-Cl(1) 113.145(16).

Accordingly, in the first step herein, THF is removed from the coordination sphere of the metal, preventing reduction of a THF solvate that may otherwise lead to the formation of cobalt oxides and other unidentified by-products. In a second step, additional DABD is added to the DABD-MCl$_2$ complex, followed by a two-electron reduction of the mixture with a reducing agent. As illustrated, the reducing agent was preferably sodium metal. However, the reducing agent may include any Group I metal such as Li, Na, K, Rb or Cs, an alkaline earth metal such Mg or Ca, main group metals such as Zn or Al, a mercury alloy of a main group metal such as Na/Hg, Li/Hg or Al/Hg, or an organometallic reducing agent such as C$_8$K, Cp$_2$Co or Cp$_2$*Co. In addition, the reducing agent may include main group hydrides such as lithium aluminum hydride and sodium borohydride to effect the indicated two-electron reduction. The final product that is formed comprises the bis-diazabutadiene metal complex ((DABD)$_2$M) wherein the yields are 85% or greater. In particular, yields upwards of 90% may be achieved when M=Fe, Co, Ni or Cr. Such yields establish the two-step synthesis as a suitable protocol for industrial scale-up. One preferred (DABD)$_2$M complex formed herein has the following structure:

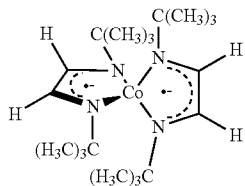

It may therefore be appreciated that in a general embodiment, the present disclosure relates to a method for forming a transition metal bis-diazabutadiene comprising the reaction in a first step, in the absence of a reducing agent, of a diazabutadiene (DABD) with a transition metal halide and forming a DABD-metal halide complex, wherein the DABD has the following structure:

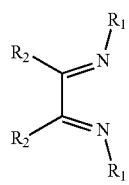

wherein R$_1$ is a C$_1$-C$_{12}$ alkyl group, amine or a C$_6$-C$_{18}$ aryl group and R$_2$ is hydrogen, a C$_1$-C$_{10}$ alkyl, a C$_6$-C$_{18}$ aryl group, amino, C$_1$-C$_{12}$ alkylamino or a C$_2$-C$_{24}$ dialkylamino group. The formed DABD-metal halide complex has the following structure:

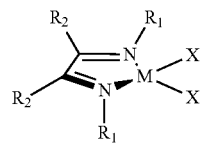

wherein R$_1$ is a C$_1$-C$_{12}$ alkyl group, amine or a C$_6$-C$_{18}$ aryl group and R$_2$ is hydrogen, a C$_1$-C$_{10}$ alkyl, a C$_6$-C$_{18}$ aryl group, amino, C$_1$-C$_{12}$ alkylamino or a C$_2$-C$_{24}$ dialkylamino group, X is Cl, Br or I and M is a transition metal. This is then followed by reacting in a second step the DABD-metal halide complex (DABD)MCl$_2$ with additional DABD in the presence of a reducing agent and forming a transition metal bis-diazabutadiene of the following structure:

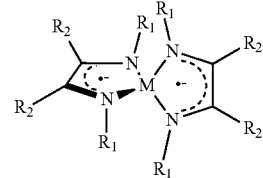

wherein R$_1$ is a C$_1$-C$_{12}$ alkyl group, amine or a C$_6$-C$_{18}$ aryl group and R$_2$ is hydrogen, a C$_1$-C$_{10}$ alkyl, a C$_6$-C$_{18}$ aryl group, amino, C$_1$-C$_{12}$ alkylamino or a C$_2$-C$_{24}$ dialkylamino group and M is a transition metal. The yield of the transition metal bis-diazabutadiene is at or greater than 85%.

Preferably, R$_1$ in the diazabutadiene ligand comprises a C$_1$-C$_{12}$ alkyl group and R$_2$ in the diazabutadiene comprises hydrogen. In addition, R$_1$ in the DABD-metal halide complex preferably comprises a C$_1$-C$_{12}$ alkyl group and R$_2$ in the DABD-metal halide complex preferably comprises hydrogen. R$_1$ in the transition metal bis-diazabutadiene preferably comprises a C$_1$-C$_{12}$ alkyl group and R$_2$ in the transition metal bis-diazabutadiene comprises hydrogen.

The transition metal halide may comprise a transition metal that is selected from Cr, Fe, Co or Ni and the halide is selected from Cl, Br or I. In particular, the transition metal halide may be Co based and the halide is Cl.

The reducing agent may preferably comprise Na, Li, Mg or Al. Sodium is particularly preferred as it is relatively easier to handle than Li, which generally requires operation under an inert atmosphere of Ar, as Li quickly reacts with most commonly used dinitrogen gas to form Li$_3$N.

The (DABD)$_2$M complexes produced herein may be advantageously utilized for ALD or CVD of a coating on a substrate. Accordingly, any substrate herein may now be coated by the (DABD)$_2$M precursor complex examples of

The invention claimed is:

1. A method for forming a transition metal bis-diazabutadiene comprising:

reacting in a first step, in the absence of a reducing agent, a diazabutadiene (DABD) with a transition metal halide and forming a DABD-metal halide complex, wherein said DABD has the following structure:

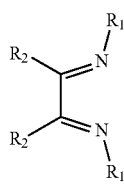

wherein $R_1$ is a $C_1$-$C_{12}$ alkyl group, amine or a $C_6$-$C_{18}$ aryl group and $R_2$ is hydrogen, a $C_1$-$C_{10}$ alkyl, a $C_6$-$C_{18}$ aryl group, amino, $C_1$-$C_{12}$ alkylamino or a $C_2$-$C_{24}$ dialkylamino group;

said formed DABD-metal halide complex has the following structure:

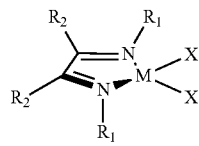

wherein $R_1$ is a $C_1$-$C_{12}$ alkyl group, amine or a $C_6$-$C_{18}$ aryl group and $R_2$ is hydrogen, a $C_1$-$C_{10}$ alkyl, a $C_6$-$C_{18}$ aryl group, amino, $C_1$-$C_{12}$ alkylamino or a $C_2$-$C_{24}$ dialkylamino group, X is Cl or Br and M is a transition metal;

reacting in a second step said DABD-metal halide complex with additional DABD in the presence of a reducing agent and forming a transition metal bis-diazabutadiene of the following structure:

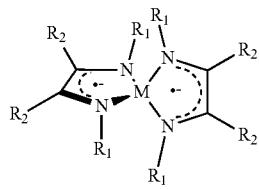

wherein $R_1$ is a $C_1$-$C_{12}$ alkyl group, amine or a $C_6$-$C_{18}$ aryl group and $R_2$ is hydrogen, a $C_1$-$C_{10}$ alkyl, a $C_6$-$C_{18}$ aryl group, amino, $C_1$-$C_{12}$ alkylamino or a $C_2$-$C_{24}$ dialkylamino group and M is a transition metal;

wherein said yield of the transition metal bis-diazabutadiene is at or greater than 85%.

2. The method of claim 1 wherein:

$R_1$ in said diazabutadiene comprises a $C_1$-$C_{12}$ alkyl group;

$R_2$ in said diazabutadiene comprises hydrogen;

$R_1$ in said DABD-metal halide complex comprises a $C_1$-$C_{12}$ alkyl group;

$R_2$ in said DABD-metal halide complex comprises hydrogen;

$R_1$ in said transition metal bis-diazabutadiene comprises a $C_1$-$C_{12}$ alkyl group; and $R_2$ in said transition metal bis-diazabutadiene comprises hydrogen.

3. The method of claim 1 wherein said transition metal halide comprises a transition metal that is selected from Cr, Fe, Co or Ni and said halide is selected from Cl, Br or I.

4. The method of claim 3 wherein said transition metal is Co and said halide is Cl.

5. The method of claim 1 wherein said DABD-metal halide complex comprises:

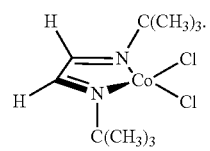

6. The method of claim 1 wherein said transition metal bis-diazabutadiene comprises the following structure:

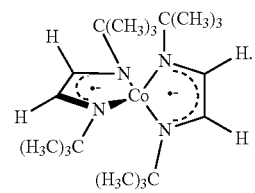

7. The method of claim 1 wherein said reducing agent comprises Na, Li, Mg or Al.

* * * * *